United States Patent [19]

Sitte et al.

[11] 4,284,894
[45] Aug. 18, 1981

[54] COLD CHAMBER FOR THE WORKING OBJECTS FOR MICROSCOPIC AND ELECTRON MICROSCOPIC INVESTIGATIONS

[75] Inventors: Hellmuth Sitte, Seefeld, Austria; Klaus Neumann, Bexbach, Fed. Rep. of Germany; Heinrich Kleber, Vienna, Austria; Helmut Hassig, Homburg-Saar, Fed. Rep. of Germany

[73] Assignee: C. Reichert Optische Werke, AG, Vienna, Austria

[21] Appl. No.: 122,215

[22] Filed: Feb. 19, 1980

[30] Foreign Application Priority Data

Feb. 17, 1979 [DE] Fed. Rep. of Germany ....... 2906153

[51] Int. Cl.³ .......................................... G01N 21/00
[52] U.S. Cl. .................................... 250/443; 250/440
[58] Field of Search ............... 250/440, 443, 442, 311; 313/11

[56] References Cited

U.S. PATENT DOCUMENTS

| 2,826,701 | 3/1958 | Columbe | 250/443 |
|---|---|---|---|
| 3,071,686 | 1/1963 | Hanggi et al. | 250/443 |
| 3,168,646 | 2/1965 | Büsch et al. | 250/443 |
| 3,171,955 | 3/1965 | Cardile | 250/443 |
| 3,373,277 | 3/1968 | Heide | 250/443 |
| 3,761,709 | 9/1973 | Hasegawa et al. | 250/443 |

*Primary Examiner*—Bruce C. Anderson
*Attorney, Agent, or Firm*—Alan H. Spencer

[57] ABSTRACT

A specimen working chamber having heat-conductive walls instead of insulative walls is disclosed.

9 Claims, 5 Drawing Figures

COLD CHAMBER FOR THE WORKING OBJECTS FOR MICROSCOPIC AND ELECTRON MICROSCOPIC INVESTIGATIONS

BACKGROUND OF THE INVENTION

This invention relates to a chamber for the preparation of specimens at reduced temperature "cryopreparation," particularly for microscopic or electron microscopic investigation.

In the cryopreparation of specimens, particularly in the cryopreparation of biological specimens for microscopic and electron microscopic studies, preparation chambers are needed to an increasing degree. Such chambers keep both the specimen and the tool at reproducible low temperatures, without icing as a result of the precipitation of atmospheric moisture. Because of the relatively high costs of the liquefied gases traditionally used as coolants ("cryogens") (particularly liquefied nitrogen=$N_2fl$ or liquefied helium=$Hefl$), the consumption of cryogen should be kept as small as possible. Finally, the cooled chamber volume should be of such dimensions that both the object in its holder as well as the necessary tools (knives, cutters, saws) and manipulation aids have adequate space in the chamber and can stay constantly in the chamber for synchronous or successive use, without interference with each other. During the preparation of biological specimens using known recrystallization phenomena of aqueous mixed phases and the development of heat associated with machining, chamber temperatures below $-150°$ C. are required. Similar temperatures are needed for machining, particularly for the preparation of sections of viscoelastic plastics with very low glass points (for example, polytetrafluoroethylene). The chamber volume should be at least one liter as a rule, with consideration of the large number of different devices.

According to the state of the art, cold chambers are made of thermally insulating plastics. For example, for taking slices from a specimen, the knife is usually fastened on the slide support of an ultramicrotome (SE Pat. No. 328 426). The knife holder is fastened to the bottom of the chamber for frozen sections. The specimen fastened on the specimen carrier arm of the ultramicrotome is introduced into the cold chamber through an opening in the rear wall, where a thin plastic film seals the opening without hindering the motion of the specimen arm necessary for the cutting. The top opening is covered over entirely or almost entirely by a cover of transparent plastic which permits observation that is absolutely necessary for manipulation. The specimen and the knife are cooled separately by a stream of cold nitrogen gas and electronic feedback control circuits make possible the control of the knife and specimen temperatures by adjusting the nitrogen flow and/or by variation of the power to heaters (cf. "Microscopy," Vol. 25 (1969), pages 17–32).

In another well known arrangement, the specimen is introduced into the cold chamber from above, while the walls consist of insulating plastic and the upper opening is not covered. A continuous adjustable flow of cold nitrogen gas from a Dewar flask regulates the temperature of the chamber atmosphere in this case, according to the signals from a temperature sensor located in the chamber. However, this simple system does not make possible a direct and/or separate preselection of the knife and specimen temperatures, which is required for several technical reasons (cf. "The Journal of Cell Biology," Vol. 51 (1971), pages 772 ff.).

It is common to most known devices that setting the temperature of the specimen and the tool (for example, the knife) is held constant by a feedback control circuit which constantly changes other decisive parameters and introduces disturbances to the system ("control oscillations"). Beyond this, the cooling is generally accomplished by gaseous nitrogen which previously had been liberated by a source of heat in the Dewar flask or recently also by a vaporizer in the cold chamber. The most significant cooling reservoir of liquefied gases, the heat of vaporization, is squandered and the consumption of the cryogen is considerable. Furthermore, the specimen and the knife in many cases are colder than the chamber atmosphere and the chamber wall. For this reason, ice forms preferentially both, since they are the "cooling poles" within the chamber, and on the outer wall of the chamber. If the cold chamber is used in combination with an ultramicrotome to prepare ultrathin slices, both the icing of the chamber and the discharge of cold nitrogen gas from the chamber interfere with the ultramicrotome parts, since changes of length are caused by the resulting temperature changes and these have a substantial effect on the uniformity of a series of slices. In chambers of the construction used for a long time, the very low temperatures (below $-150°$ C.) required for biological cryopreparations cannot be reached or can be reached only for a very short time by the use of a very high consumption of gaseous nitrogen as a coolant.

PRIOR ART

U.S. Pat. No. 2,816,232 issued Dec. 10, 1957 discloses a container for holding a substance at cryogenic temperatures. The unit has an inner container surrounded by an outer container and the containers are disclosed as being made of materials of low heat conductivity.

British Pat. No. 955,320 published Apr. 15, 1964 discloses a vacuum flask container for a cryogen having a small article compartment therein. The compartment is in direct contact with the cryogen.

German Auslegeschrift No. 20 10 967 discloses a multiple chamber cryogenic container.

SUMMARY OF THE INVENTION

The purpose of this invention, therefore, is to provide a cold chamber similar to the type initially described which does not have the defects mentioned above; with a comparatively simple mechanical structure; without complicated electrical feedback control circuits; which permits the realization of temperatures below $-150°$ C. under reproducible conditions; without restraint on free and independent selection of the parameters; and maintaining a moderate cryogen consumption.

In accordance with the invention, this problem is solved by providing that the interior side walls and the interior bottom of the chamber—in contrast to the state of the art—of sheet metal with good heat conductivity, can be held at constant temperature by a fluid cryogen during the entire operation. The cryogen can directly contact the outside surfaces of the sheet metal which forms the chamber wall, if the chamber wall is part of a cryogen tank. If the cold chamber is used independently of other apparatus, as is frequently the case, the inner chamber can be formed as a sheet metal box placed in a larger sheet metal box in such a way that the cryogen contained in the larger box, liquid nitrogen ($N_2fl$), for example, flows around the bottom and the four side walls of the rectangular cold chamber and thereby guarantees a very uniform temperature of the chamber walls and as a further consequence, of the chamber atmosphere. If the cold chamber is used in combination with another apparatus, a microtome, for example, at least two side walls can be similarly cooled directly and symmetrically by two fastened cryogen tanks, wherein a pipe can make a cryogen communication between the two separate tanks to simplify the filling of the tanks. By using sheet metal with good heat conductivity, very low chamber temperatures can also be reached in this way. Also, the chamber walls can be cooled down by cooling coils which lie directly against the chamber wall and makes good thermal contact with it. The tube system can be cooled by liquid cryogen in a manner also well known. In the higher temperature region, for example, the connection to a cooling thermostat of known construction is also possible, combined with cryogen circulation through a pump. If liquefied gas is used as a cryogen, the heat of vaporization is used primarily for the cooling of the cold chamber in the systems described in accordance with the invention. The consumption of cryogen of the system pursuant to the invention is therefore lower than the consumption of the prior art commercial cold chambers by a factor of approximately 0.5 to 0.1.

If the chamber atmosphere and/or separate chamber parts is desired to have a particularly low temperature, for example, of the specimen or of a specific machining tool, the system can be constructed and can operate in two stages pursuant to the invention. For example, this can be accomplished by providing another sheet metal chamber inserted in a chamber of the type described above, wherein the inner chamber, as the second stage, is cooled with a cryogen whose boiling point is lower than that of the cryogen which cools the outer chamber. However, it is also possible merely to cool down a portion of the system located in the chamber by means of a flow of a cryogen of lower temperature below the temperature of the chamber atmosphere. Of course, it is compulsory in this case to flush the sections cooled to lower temperatures, as a rule the entire inner chamber, with helium gas, if for example, liquid helium ($He_{fl}$) if used for cooling, in order to suppress a condensation of nitrogen and oxygen on the chamber sections cooled to the lower temperature. The flushing with gas is done in this case pursuant to the invention independently of the cooling using a gas that is dried and cooled down to the temperature of the chamber atmosphere before its entrance into the chamber.

The temperature setting of the specimen as well as that of the tools required for the machining and manipulation of the specimen, if necessary individually, is made by heating and cooling devices. The heating elements can either provide the maximum heat for the rapid elevation of the temperature, or a lower heat associated with a specific temperature for the maintenance of specific temperatures in equilibrium. In this case, if the output temperature of the element is below the desired temperature, the maximum heating power is initially set. As soon as the desired temperature is reached, a shift to a "steady state power" occurs, which in contrast to feedback control circuits guarantees adequate temperature stability of the element without interfering control oscillations. Conversely, if the output temperature is above the desired temperature, the element is brought into thermal contact with a metallic cooling device, which in turn has a broad surface contact with the chamber wall and has high heat capacity in comparison with the element in question. Contact is maintained until the element has reached the desired lower temperature. Thereafter, the contact is broken and the heat again is set at the steady state value for the desired temperature. In this way, the desired temperature can be obtained rapidly and can thereafter be kept sufficiently constant without oscillations. Values obtained in this way are approximately 20° C. above the temperature of the metallic chamber walls, which in the case of $N_2fl$ cooling, is approximately $-175°$ C. If lower temperatures are needed, a direct thermal connection to the chamber wall, through a flexible copper braid is useful.

It has been found from experience that thermal insulation of the conventional thickness in the range of about a centimeter in normally humid room air cannot prevent the formation of water of condensation or deposits of ice. In accordance with the present invention, this can be eliminated by surrounding the outside of the thermal insulation (polystyrene foam, for example) with a thermostatically heated metallic jacket. This jacket can also serve to heat the gas to be evaporated when cooling with liquefied gases (e.g., $N_2fl$) which is discharged either through openings in the heated jacket, or simply between the inner jacket wall and the insulation. The low temperature region is limited in this way to the chamber itself. Also, in accordance with the invention, a system of openings can be provided in the jacket, which permit specimens and equipment to be introduced from the side into the chamber or to be removed from the chamber with a constant, reliable seal of the chamber against loss of the extremely cold chamber atmosphere. The chamber thereby becomes compatible with all current cryotransfer systems.

Finally, a combination of the variations of embodiment described above with one another, as well as the combination of these variations with technologically known systems, also lie within the scope of the invention. Thus, for example, the filling of the cryogen tanks can be accomplished by automatic systems, and the indication of the level of filling can be accomplished by level sensors and light-emitting diodes, or in other known ways. Furthermore, the concept of the invention is not affected by the type, number, and particular arrangement of the specimens and equipment for the specimen preparation. Finally, if the particular type of preparation work to be carried out and the instrumentation necessary for it permits, the chamber can be covered entirely or partly to reduce the heat exchange and possibility of convection, and the deposition of frost associated therewith.

BRIEF DESCRIPTION OF THE DRAWINGS

Further benefits and features of the invention follow from the description below of prefered embodiments with the use of the attached drawings. The drawings show.

THE PREFERRED EMBODIMENTS

Figure 1:
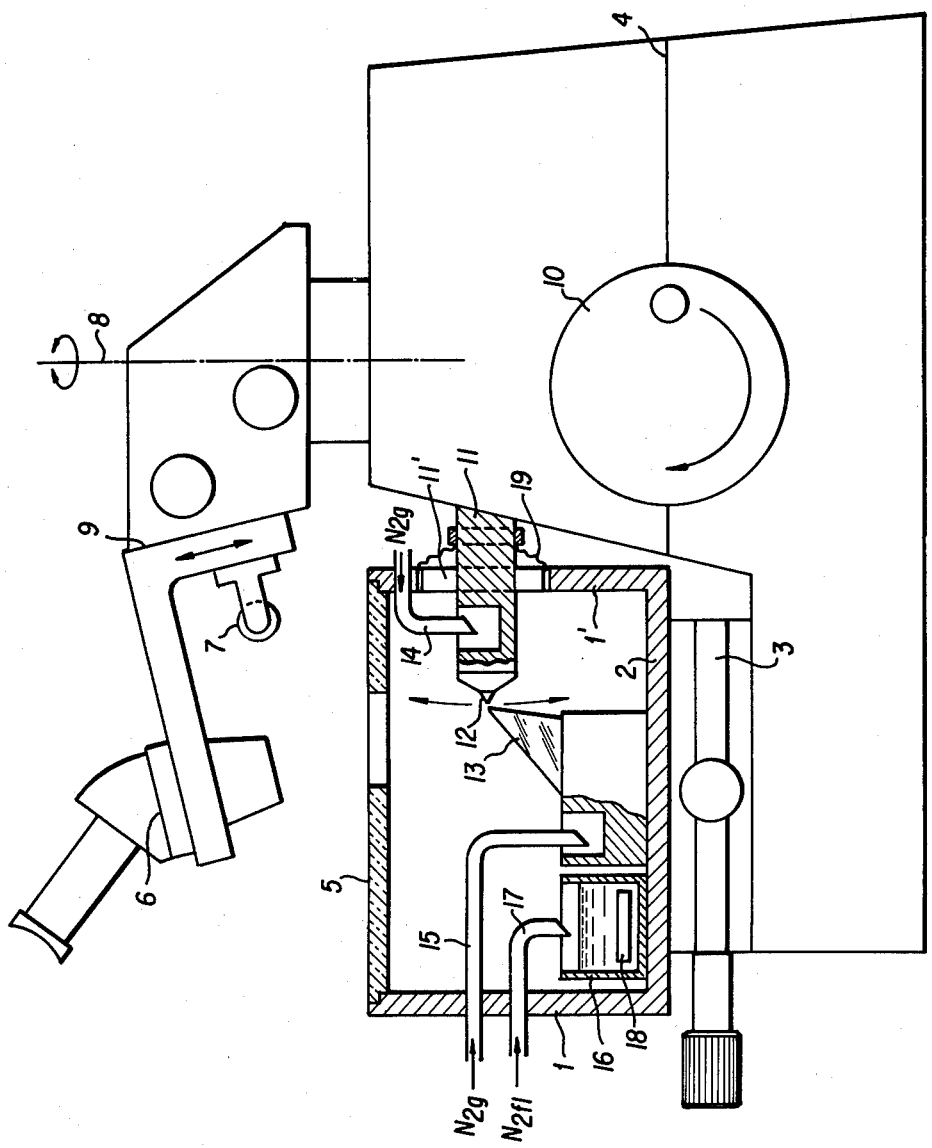
FIG. 1 is a schematic side view, partially in section, of a cold chamber for an ultramicrotome in accordance with the state of the art.

The construction of the cold chamber shown in FIG. 1 on an ultramicrotome is of a traditional type. Side walls 1, 1', and bottom 2 which consist of a plastic with poor heat conductivity of the cold chamber are fastened to sliding support 3 which is mounted on the base of the ultramicrotome 4. The top chamber opening is largely covered over by transparent plastic cover 5 which leaves only slits for the observation of the cutting process with a stereomicroscope 6, which together with a cold light source 7, is fastened above an optics carriage 9, which can be shifted in the directions of the arrows as well as rotated around the axis 8.

Specimen carrier arm 11 with specimen 12 fastened to it can be moved in a pivoting up-down motion by rotating a hand wheel 10 or by a built-in motor drive (not shown), whereby a conventional feed mechanism of the ultramicrotome brings about the removal of slices at the knife 13 when the specimen moves downward, and a withdrawal of the specimen away from the cutting knife during the upward motion. The special holders of specimen 12 on specimen carrier arm 11 and of knife 13 on chamber bottom 10 can each be cooled individually and independently of one another by a stream of cold nitrogen gas ($N_2g$) from feed tubes 14 and 15, respectively. In a manner not illustrated but well-known, the temperatures of specimen 12 and knife 13 can be measured with the use of sensors which are located in the respective holder. The temperature of the holder can be raised by cartridge heaters which are located in the holders. The cartridge heaters and the temperature sensors and/or valves or vaporizers regulating the nitrogen flow are well known and adjust the temperature of specimen 12 and of knife 13 to preselected desired values. In addition, the temperature and composition of the chamber atmosphere can be influenced by vaporization of $N_2fl$ fed into plastic container 16 through feed line 17, by means of blade heater 18. Discharge of the cold chamber atmosphere through opening 11' upon insertion of specimen carrier rod 11 into rear wall 1' of the cold chamber is prevented by thin film 19 (SE Pat. No. 328 426, "Microscopy" loc. cit.), which adequately seals the gap between specimen carrier arm 11 and chamber wall 1', and which also offers no interfering resistance to the motion of specimen carrier arm 11 even at low temperatures, because of its minimal thickness. Similar cold chambers operate in principle in similar manners, but independently of microtomes or ultramicrotomes, for the machining of specimens for microscopic or electron microscopic investigation, particularly for the cryofixation of biological specimens on extremely cold metal surfaces, and for machine cutting of extremely cold biological or industrial samples.

Figure 2:
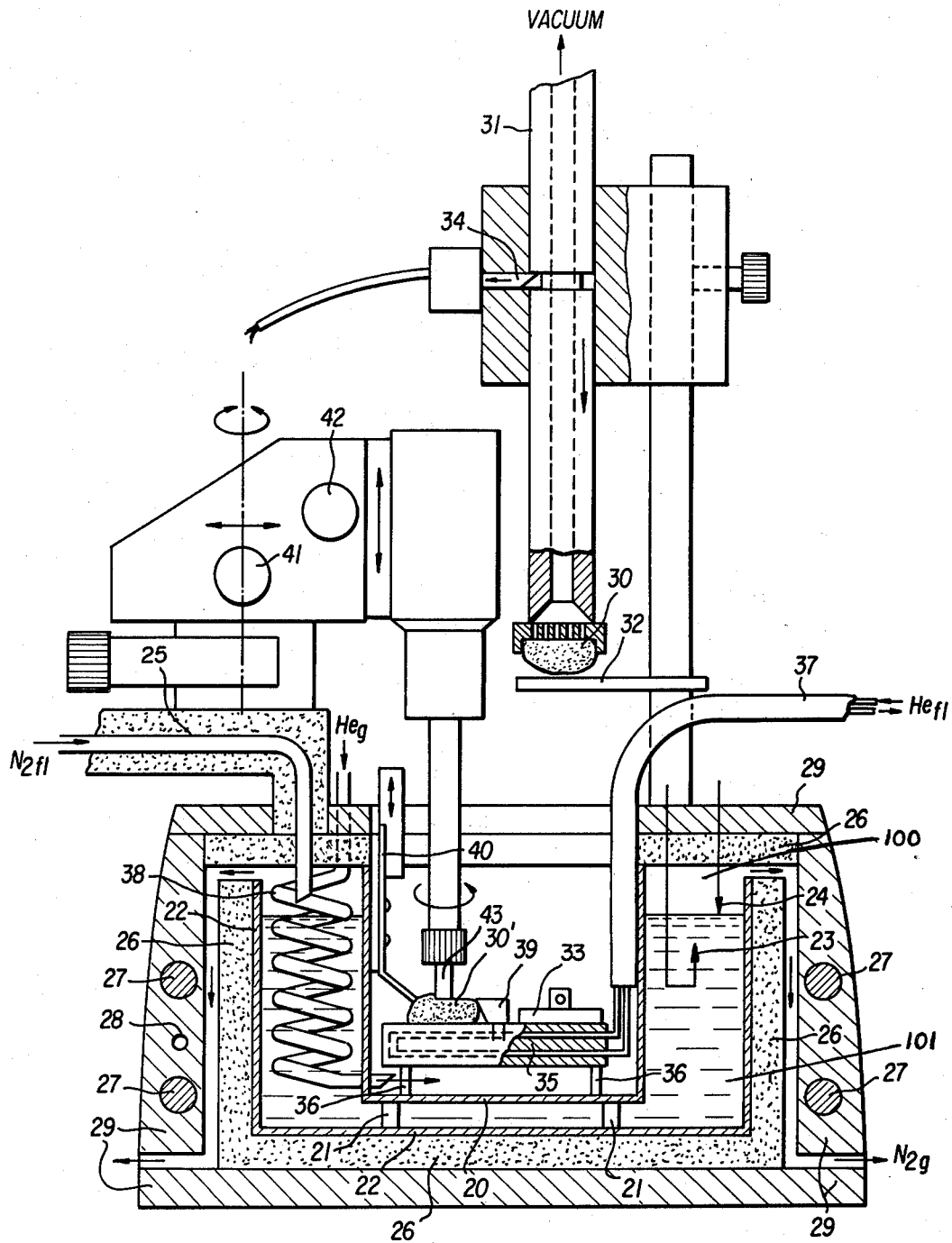
FIG. 2 is a schematic cross section in front view of a cold chamber pursuant to the invention in equipment for the cryofixation and machining of cryogenically fixed specimens with $He_{fl}$ cooling of the metal device and helium gas flushing of the chamber.
Figure 3A:
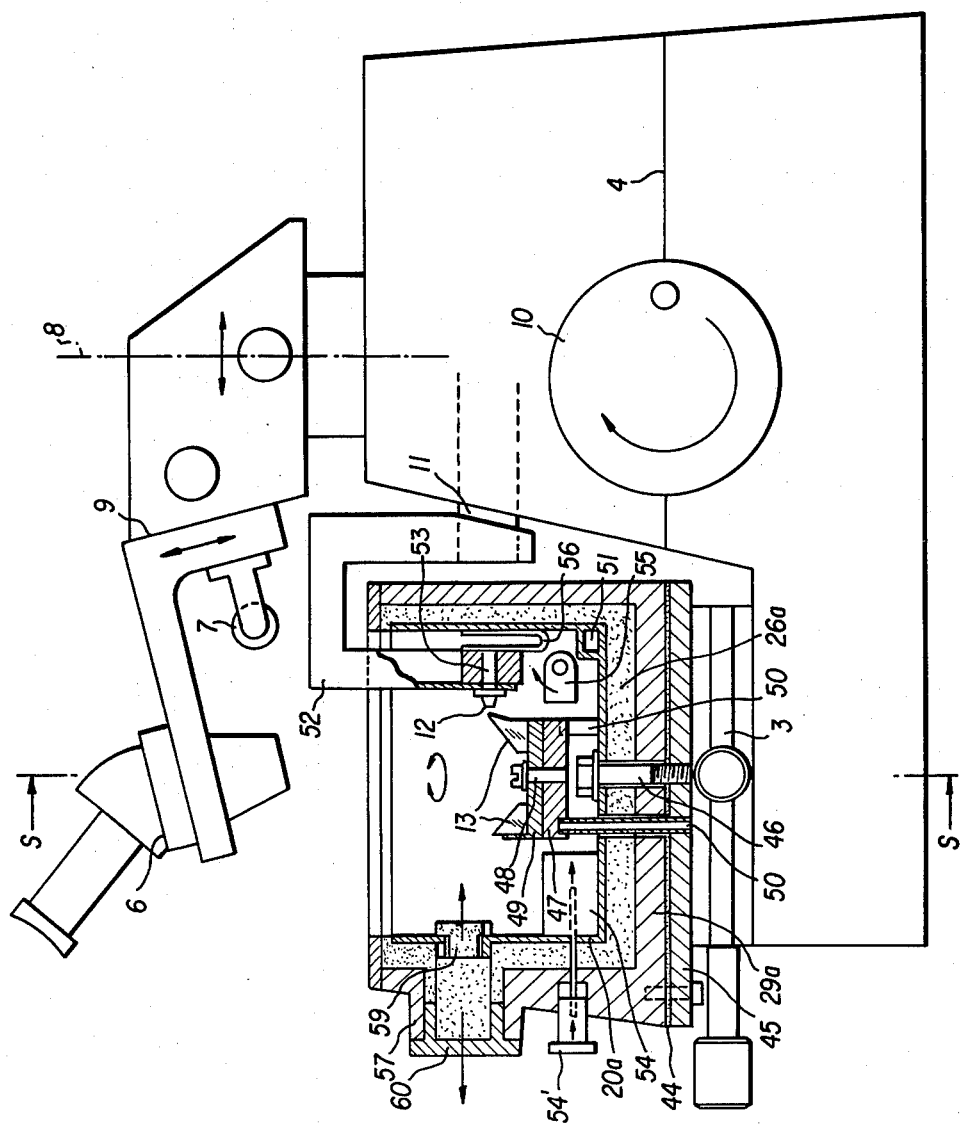
FIG. 3a is a side view.
Figure 3B:
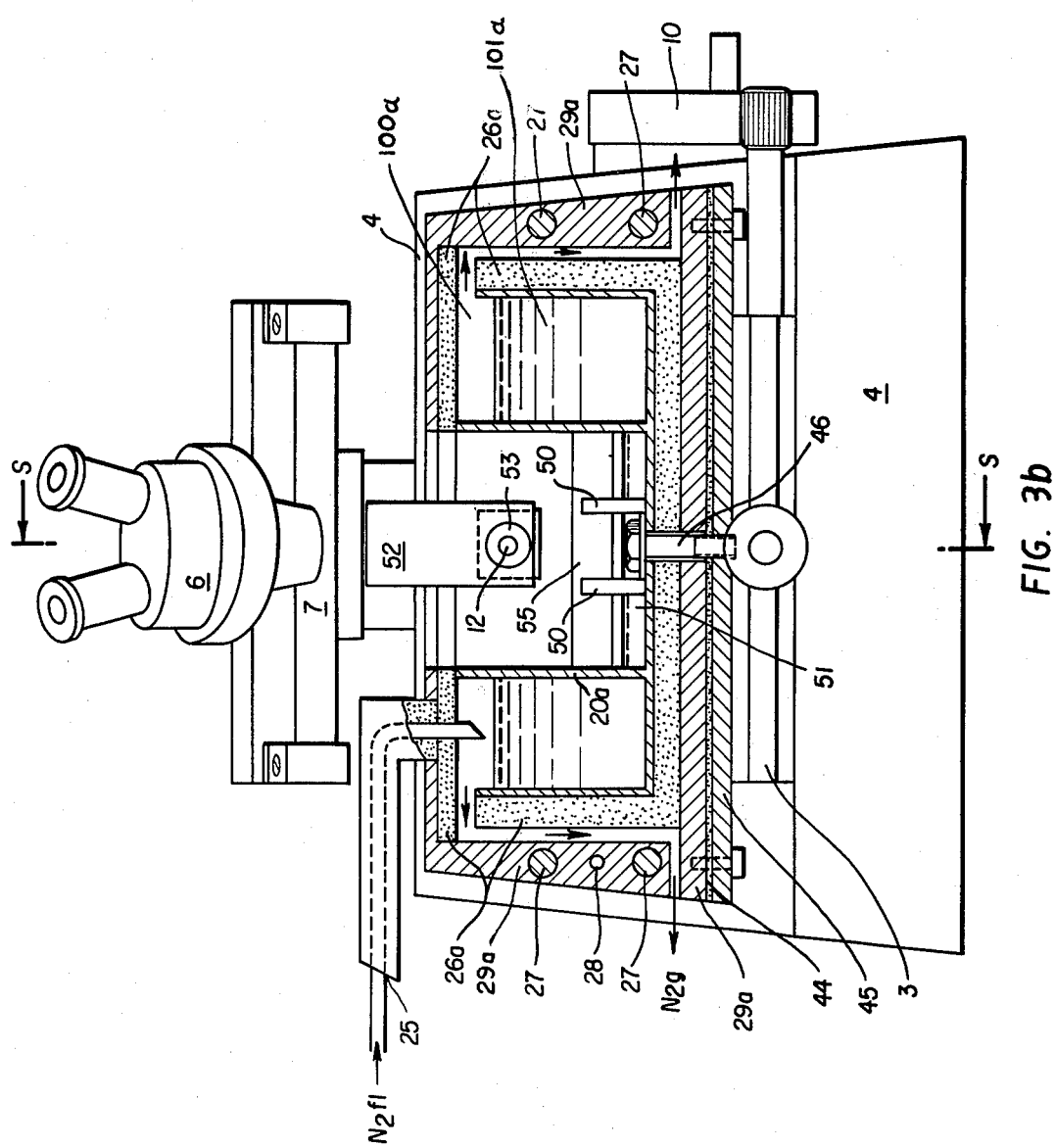
FIG. 3b is a front view in schematic cross section of another cold chamber pursuant to the invention for an ultramicrotome, wherein the knife holder is removed in FIG. 3b.
Figure 4:
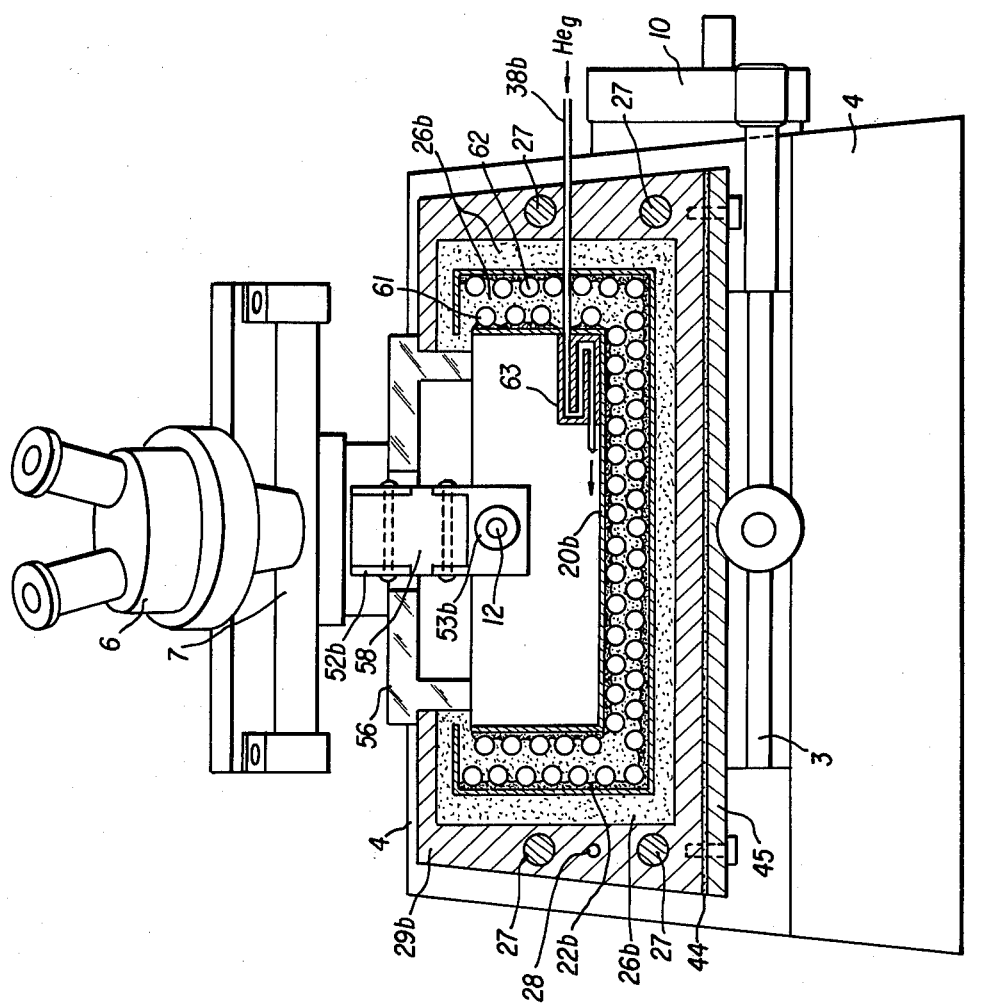
FIG. 4 is a schematic front view, partially in ross section, of a cold chamber operating in two stages with helium gas flushing on an ultramicrotome.

FIGS. 2 to 4 show possible embodiments of cold chambers in accordance with the invention which can be used, for example, for specimen 12 and knife 13 of ultramicrotome 14 in accordance with FIG. 1, but independently of a microtome or ultramicrotome, for other supplementary equipment.

The cold chamber pursuant to the invention in accordance with FIG. 2 has rectangular case 20 open at the top and made of sheet metal with good heat conductivity. Case 20 is fastened through feet 21 to rectangular container 22 which is also made of sheet metal and is open at the top. Case 20 and/or container 22 can also be made of another suitable material impervious to cryogen and able to withstand low temperatures. Space 100 which is between case 20 and container 22, is filled with cryogen 101 ($N_2fl$, for example) up to the indicated level. The regulation of level of cryogen 101 is controlled by sensors 23 and 24 and replacement takes place through insulated cryogen feed line 25. Large losses of cryogen or heat are prevented by insulation 26, preferably of foamed plastic, and icing of outer wall 29 is prevented by using a metal with good heat conductivity and heating wall 29 to room temperature by means of cartridge heater 27 and controlled temperature sensor 28.

The embodiment pursuant to FIG. 2, in addition, shows special equipment for rapid freeze-drying ("cryofixation") and for the subsequent machining of frozen biological specimens. Injector 31 equipped with a vacuum chuck, is used to hold the object, and enters the cold chamber automatically with specimen 30 after removal of heat-protective shield 32 and of frost-protective cover 33, by releasing safety catch 34. The specimen first strikes the highly polished surface of metal block 35 which is heat conductively connected to the bottom of chamber 20 through feet 36. If the cryofixation is to take place at the temperature of the cryogen surrounding case 20 ($N_2fl$, for example), the normal cooling of metal device 35 through feet 36 and through the chamber atmosphere is sufficient. If a cryofixation is necessary at an even lower temperature, cooling body 35 can be cooled by circulating liquid helium ($He_{fl}$), for example, through insulated double line 37, and metal body 35. Deposits of frozen oxygen and nitrogen are prevented by continuous flushing of case 20 with helium gas ($He_g$), which is precooled and dried in conduit 38. Deposits on the highly polished cooling surface of metal body 35 are avoided by cover 33 which is only removed briefly before the injection of specimen 30. After cryofixation, frozen specimen 30' can be held, for example, by fixed holder 39 combined with adjustable holder 40. Excess material of specimen 30' is removed by motor-driven cutter 43 which is driven through drive train 41 and 42 in preparation for subsequent operations (removal of slices in the cold chamber of an ultramicrotome, freeze-etching and duplication, cryosubstitution, freeze-drying). In all of the cases mentioned, the success of the subsequent preparation depends on the fact that the volume of the specimen is limited to the smallest size absolutely necessary, and if need be, is reduced by splitting at low temperature with a saw, not illustrated, if possible to below 10 mm³.

The embodiment of the invention shown in FIGS. 3a and 3b makes possible the mounting of the cold chamber on slide support 3 of ultramicrotome 4. Thermostatically heated outer chamber wall 29a is bolted through flexible interlayer 44 to support plate 45 which in turn is rigidly fastened to slide support 3. The chamber is held against support plate 45 by bolt 46.

The knife holder consists of base 47 and plate 49, which is rotatable around pivot 48. Several different knives 13 can be interchanged with one another by rotating plate 49 without changing the temperature if it is necessary for the precutting ("trimming") and ultrathin sectioning (sometimes optionally diamond and glass knives). Knife holder 37, 48, and 49 is fastened on three supports 50 which in turn are rigidly connected to support plate 45. The discharge of cold chamber atmosphere through the openings provided for supports 50 and for fastening bolt 46 is prevented by elastic interlayer 44, which serves as a seal on the one hand and protects the knife from forces acting on the chamber during the cutting process, in the manner of a "stressed-skin construction" (AT Pat. No. 320 308, article on "New Possibilities With Ultramicrotomes" in Laboratory Practice in Medicine, Nov. 78, pp. 26 ff.). Chamber walls 20a are cooled by the cryogen, $N_2fl$, for example, contained in two spaces 100a located symmetrically on the two long sides. The two spaces communicate through cross connection 51. The front and rear wall and the bottom surface of the cold chamber also connect to spaces 100a. These parts are surrounded by foam insulation 26a and the thermostatically heated outer jacket 29a.

Both knife holder 47, 48, 49, and specimen holder 53 which is mounted on a Christenson bridge 52 with thermal insulation can be rapidly cooled from high to low temperatures by cooling bodies 54 or 55. For this purpose, in cooling the knife, cooling block 54 resting on the chamber floor is shifted in the direction of the arrow by means of slide 54', until it contacts knife holder component 47. In the same way, cooling block 55 can be rotated by hand wheel 10a in the direction of the arrow, so that it comes into thermal contact with the bottom of specimen holder 53 to cool specimen 12. Since cooling blocks 54 and 55 have substantially higher heat capacities than the specimen and knife holders and are in permanent surface contact with side walls 20a of the cold chamber, the thermal contact brings about a rapid cooling of specimen 12 and knife 13. If the specimen takes up too much heat through ridge 52 in the normal flow balance, a direct thermal contact with the chamber wall can be made by flexible copper braid 56, which shifts the equilibrium to a lower temperature range.

Outer wall 29a of the chamber can have passage 57 on the front, for example. Passage 57 can simply be sealed by two plugs 59 and 60 from the inside as well as from the outside. Specimens or specimen parts can be introduced into the chamber or slid out of the chamber without the loss of cold chamber air to any disturbing extent by successively opening and closing the plugs.

In contrast to the preceding FIGS. 2 and 3, FIG. 4 shows a cold chamber constructed and operating in two stages, whose cooling is accomplished not through cryogen tanks, but by means of circulatory cooling. In outer jacket 29b, in this case are located two sheet metal cases 22b and 20b which are cooled to different temperatures by tube systems 61 and 62 lying against them in good thermal contact with the sheet metal, through which a cryogen is circulated. The wall of outer sheet metal case 22b here is cooled by a cryogen with higher boiling point ($N_2fl$, for example), while the wall of the inner case 20b is cooled by one with a lower boiling point ($He_{fl}$, for example). The space between sheet metal case 22b and the thermostatically heated outer jacket 29b, is filled with polystyrene foam or in a similar material 26b, or is thermally insulated in another way.

Beside the feed lines and discharge lines for $N_2fl$ and $He_{fl}$, not illustrated in FIG. 4, feed line 38b is provided for flushing the chamber with helium gas ($He_g$), wherein the $He_g$ is cooled in a known manner in heat exchanger 63 and is freed of the last traces of moisture.

The heat supply through the bridge can be reduced considerably by making no continuous metallic contact between the specimen carrier arm and specimen 12. Specimen holder 53b is separated from bridge section 52b by insulator 58 (for example, molded polystyrene) of sufficient cross section to prevent any great heat transfer. In the same way, with respect to the lower chamber temperature, any great heat transfer through the top chamber opening is prevented by cover 5b.

The chamber arrangement pursuant to FIG. 4, because of the elimination of the bulky cryogen tanks, offers the advantage in comparison with other embodiments of a more favorable ratio between the chamber inner volume and the chamber outer volume, which can be important in the mounting of the cold chamber on slide support 3 of ultramicrotome 4.

The devices described with the use of FIGS. 2 to 4 can be realized in different variations and combinations within the scope of the invention. Thus, for example, it is possible to make the circulatory cooling with liquid cryogen described in FIG. 4 with one stage, as well as without helium flushing of the chamber, or to consider the thermal partition between bridge 52b and specimen holder 53b also in working in the higher temperature regions. In the same way, it is possible in a technologically known manner to use partially solidified nitrogen ("$N_2$ slush") as the cryogen in the tanks, at a temperature of $-210°$ C. The type and manufacture of the foam insulation can also be varied in known ways, as can the mounting of the chamber on the ultramicrotome support and the mounting of the specimen and knife. For example, all parts of the specimen holder or knife holder heated above the temperature of the chamber atmosphere, and tools and equipment also heated in the same way, can, to some extent, be coated with an appropriate insulation, for example, a thin polystyrene layer, to avoid interfering thermal convection flow in the chamber atmosphere. Finally, it is immaterial in what way the electrical temperature adjustment of the chamber outer wall takes place, as well as what additional equipment is used in such chambers, and what apparatus is operated in combination with such cold chambers for the preparation of specimens for a microscopic or electron microscopic investigation.

What is claimed is:

1. A chamber for working specimens at cryogenic temperatures which comprises:
    a compartment having a bottom and sidewalls providing space for working the specimens, said bottom and sidewalls being heat-conductive,
    an exterior jacket,
    an insulating liner separating said compartment from said jacket,
    a cover for said compartment, and
    a plural cryogen system, said system having a first cooling means containing a first liquid cryogen for cooling a first portion of said chamber, the first liquid cryogen having a first temperature, a second cooling means containing a second liquid cryogen for cooling a second portion of said chamber, the second liquid cryogen having a second temperature, said first temperature being lower than said second temperature, said first portion being proximate to the specimens and said second portion surrounding a substantial part of said first portion.

2. The chamber of claim 1 wherein said first cooling means includes a first length of heat-conductive tubing to provide a continuous passage for said first cryogen.

3. The chamber of claim 2 wherein said second cooling means includes a second length of heat-conductive tubing to provide a continuous passage for a second cryogen.

4. The chamber of claim 1 further including at least one heat-conductive mass in contact with at least one of said bottom and sidewalls, said mass being selectively positionable in heat transferring contact with a tool being used in said chamber.

5. The chamber of claim 3 wherein an insulating means separates said first and second lengths of tubing.

6. The chamber of claim 1, 2, 3, 4 or 5 wherein said jacket is heat-conductive and has heaters to maintain the jacket at room temperature.

7. The chamber of claim 1, 2, 3, 4 or 5 further including a passage, said passage extending through said jacket, insulating liner and a sidewall, an insulating plug means to temporarily seal said passage, whereby specimens may be introduced into and removed from said compartment through said passage.

8. In combination, a microtome having a specimen arm, a knife, a base and a chamber for working the specimen at cryogenic temperatures mounted on said base, said chamber comprising:

a compartment having a bottom and sidewalls providing space for working the specimens, said bottom and sidewalls being heat-conductive,
an exterior jacket,
an insulating liner separating said compartment from said jacket,
a cover for said compartment, and
a plural cryogen system, said system having a first cooling means containing a first liquid cryogen for cooling a first portion of said chamber, the first liquid cryogen having a first temperature, a second cooling means containing a second liquid cryogen for cooling a second portion of said chamber, the second liquid cryogen having a second temperature, said first temperature being lower than said second temperature, said first portion being proximate to the specimens and said second portion surrounding a substantial part of said first portion.

9. The combination of claim 8 wherein said base includes adjustable slide means, said chamber being mounted on said slide means and said knife being mounted in said compartment to permit movement of the knife relative to the specimen arm.

* * * * *